United States Patent
Leahey

(10) Patent No.: US 7,141,097 B2
(45) Date of Patent: Nov. 28, 2006

(54) BACTERIAL RETENTIVE, AIR VENTING, INTRAVENOUS FILTER

(75) Inventor: John A. Leahey, Woodstock, IL (US)

(73) Assignee: Filtertek Inc., Hebron, IL (US)

( * ) Notice: Subject to any disclaimer, the term of this patent is extended or adjusted under 35 U.S.C. 154(b) by 123 days.

(21) Appl. No.: 10/755,980

(22) Filed: Jan. 13, 2004

(65) Prior Publication Data
US 2004/0226444 A1    Nov. 18, 2004

Related U.S. Application Data

(60) Provisional application No. 60/440,106, filed on Jan. 15, 2003.

(51) Int. Cl.
*B01D 19/00* (2006.01)

(52) U.S. Cl. ............... 96/6; 95/46; 604/126; 604/406; 210/321.64

(58) Field of Classification Search ............ 96/6; 95/46; 604/406, 6.09, 126; 422/44; 210/321.64, 210/321.75, 321.84, 436, 645, 472, 455
See application file for complete search history.

(56) References Cited

U.S. PATENT DOCUMENTS

| | | | | |
|---|---|---|---|---|
| 4,294,594 A | * | 10/1981 | Sloane et al. | 96/6 |
| 4,525,182 A | * | 6/1985 | Rising et al. | 96/6 |
| 5,348,646 A | | 9/1994 | Costello, Jr. et al. | 210/94 |
| 5,439,587 A | | 8/1995 | Stankowski et al. | 210/321.64 |
| 5,827,429 A | * | 10/1998 | Ruschke et al. | 210/321.75 |
| 6,347,711 B1 | * | 2/2002 | Goebel et al. | 210/436 |
| 6,508,859 B1 | * | 1/2003 | Zia et al. | 95/46 |

FOREIGN PATENT DOCUMENTS

EP     0 302 722 A2    2/1989

OTHER PUBLICATIONS

*Filtration Solutions, for the health care industry,* Gelman Sciences, Products Pamphlet, undated but prior to Jan. 15, 2003, 6 pages.

* cited by examiner

*Primary Examiner*—Duane Smith
*Assistant Examiner*—Douglas J. Theisen
(74) *Attorney, Agent, or Firm*—Steven P. Shurtz; Brinks Hofer Gilson & Lione

(57) ABSTRACT

A filter for filtering intravenous fluid includes a base member having one or more vent holes and a fluid inlet chamber; a cap member having an inlet, an outlet, and a fluid outlet chamber; hydrophilic filtration media captured between the base member and the cap member, separating the inlet chamber and the outlet chamber; the filter having a flow path such that fluid passing into the filter housing through the inlet passes through the hydrophilic filtration media before passing out the outlet; one piece of hydrophobic vent media positioned over the vent hole and secured to the base member; and the base member having a center section and side sections forming the inlet chamber, the side sections extending from the center section towards the perimeter of the base member and being formed with sloped walls so as to encourage any air in the inlet chamber to flow towards the vent.

21 Claims, 5 Drawing Sheets

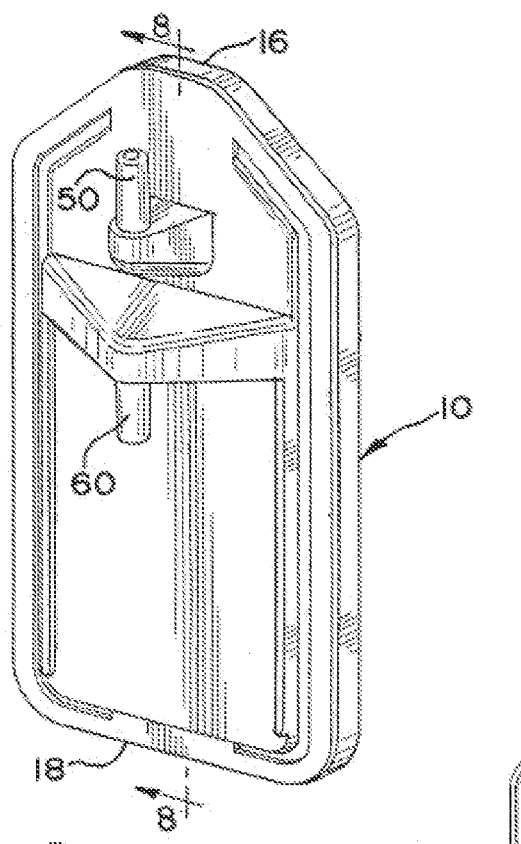
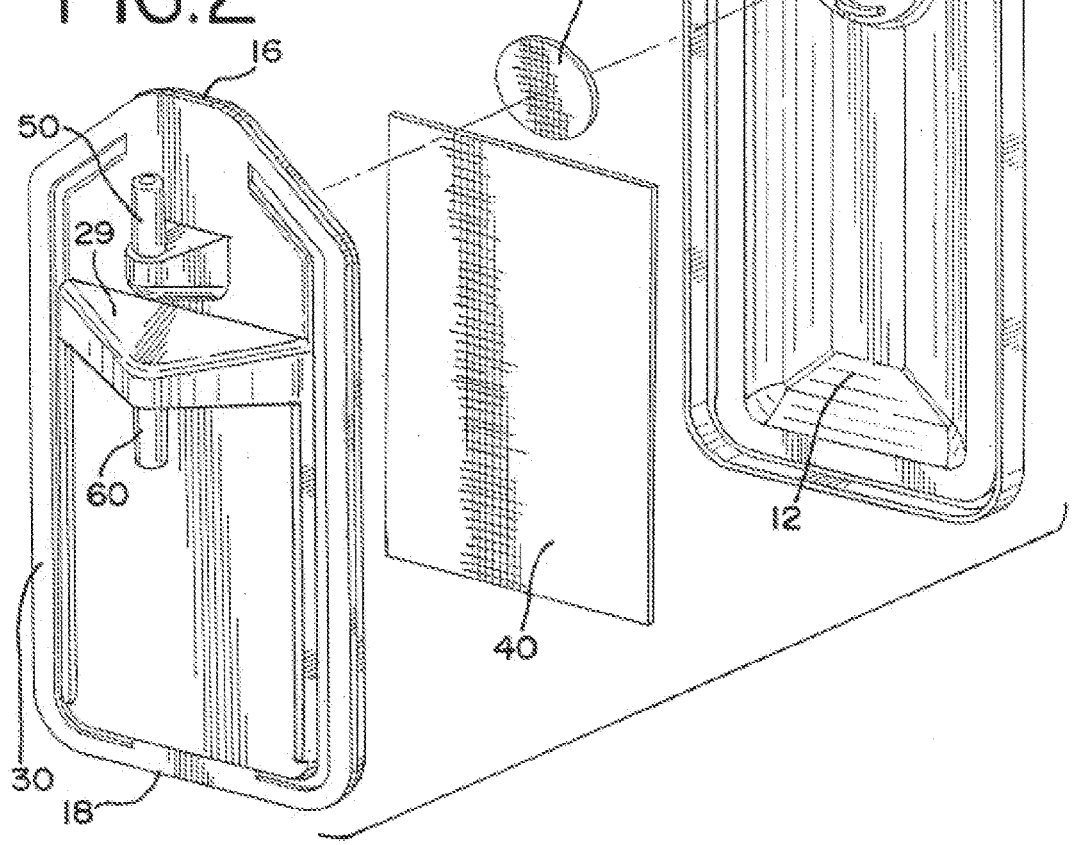

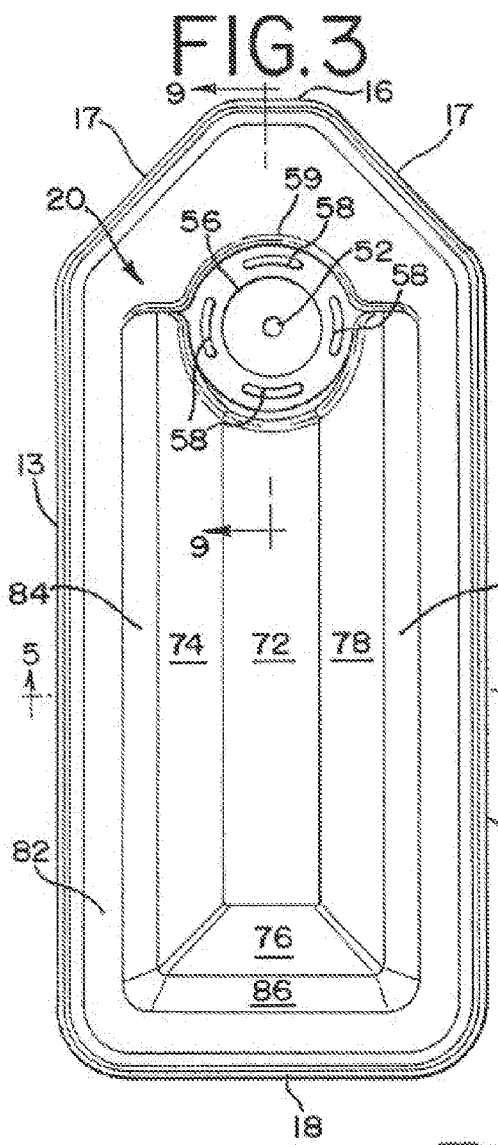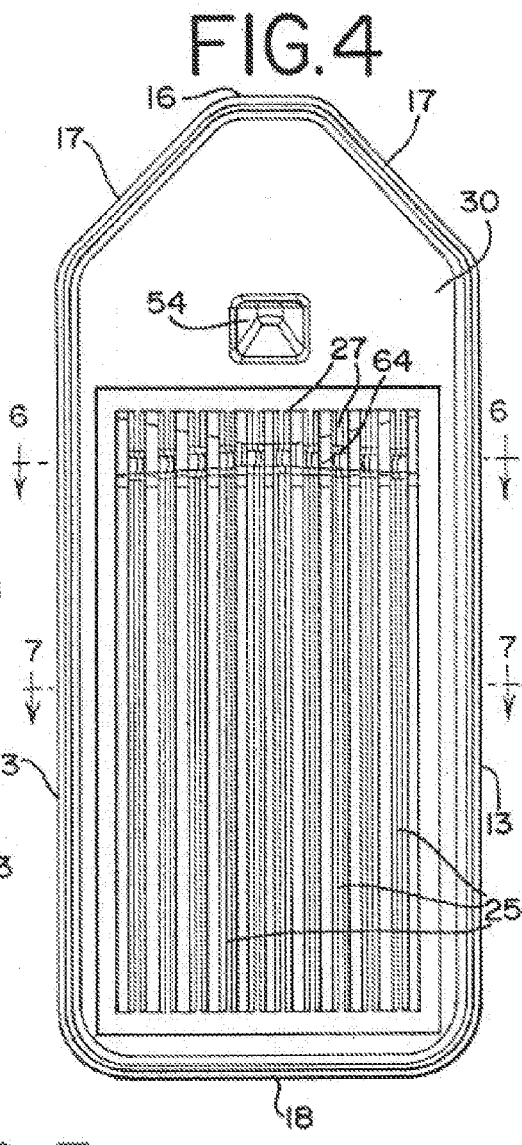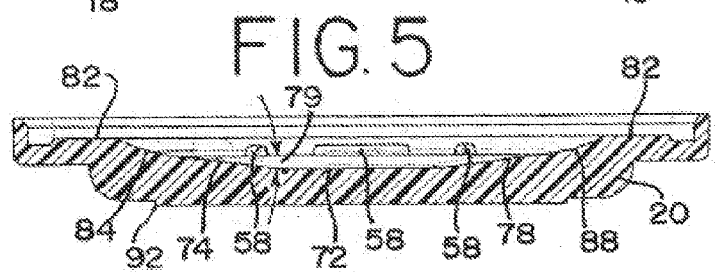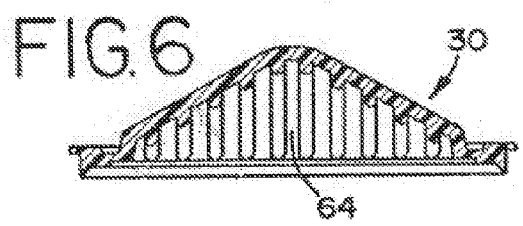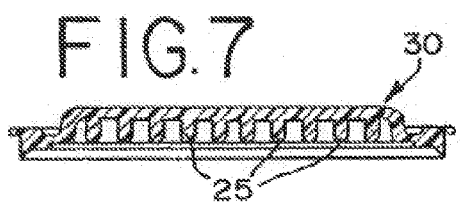

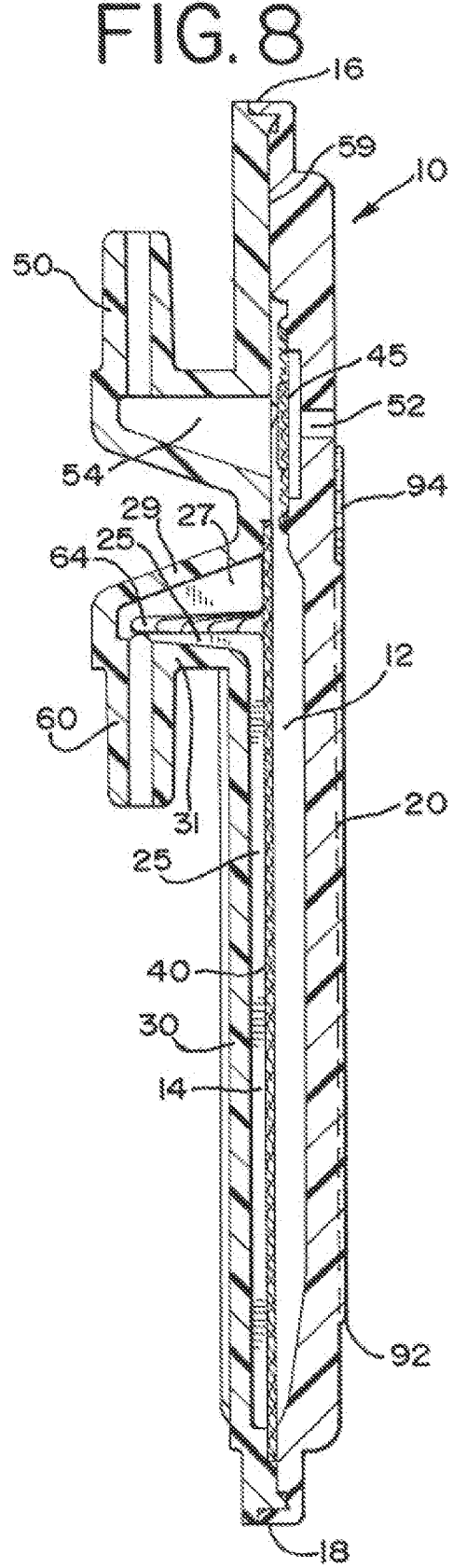
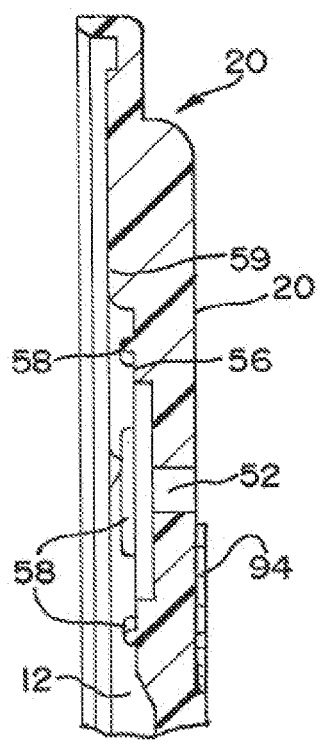

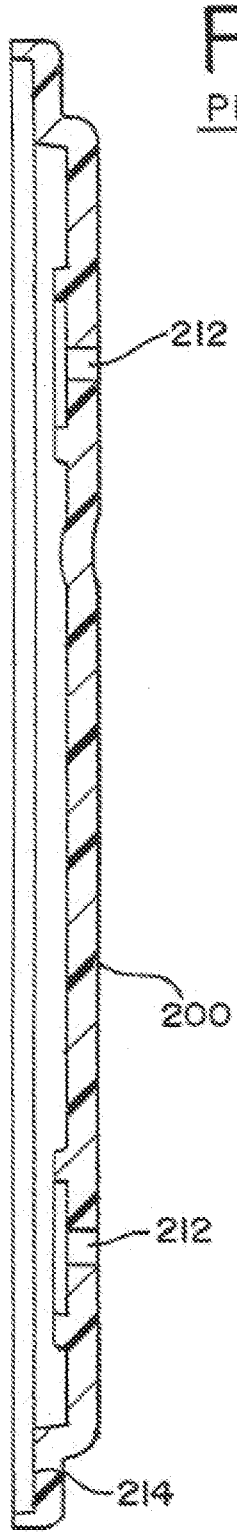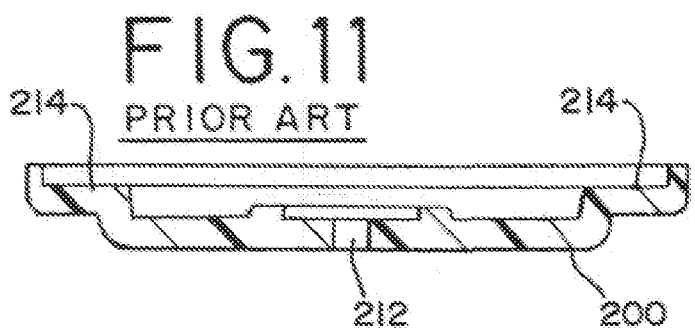
FIG. 10 PRIOR ART
FIG. 11 PRIOR ART

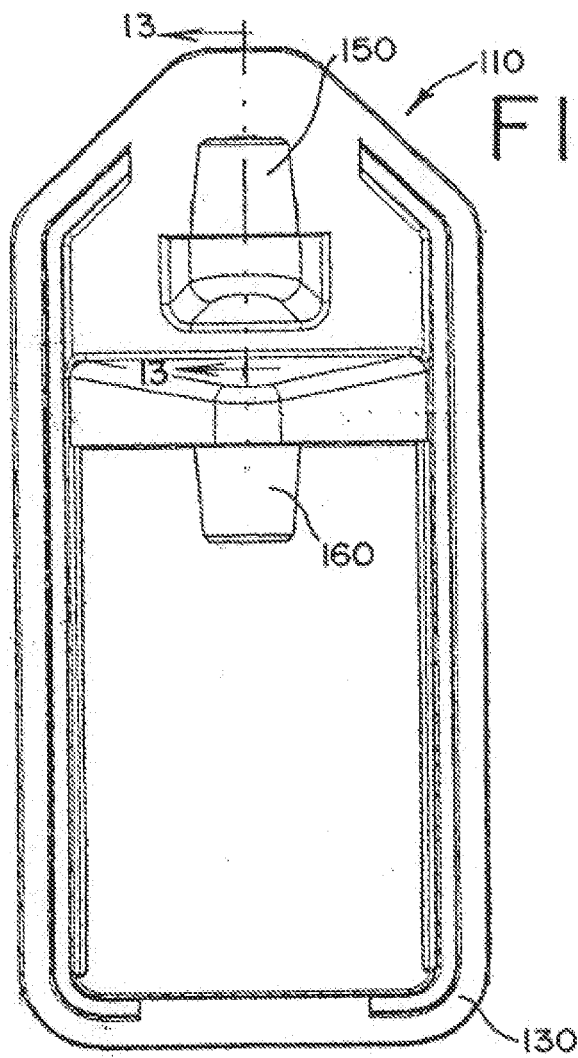
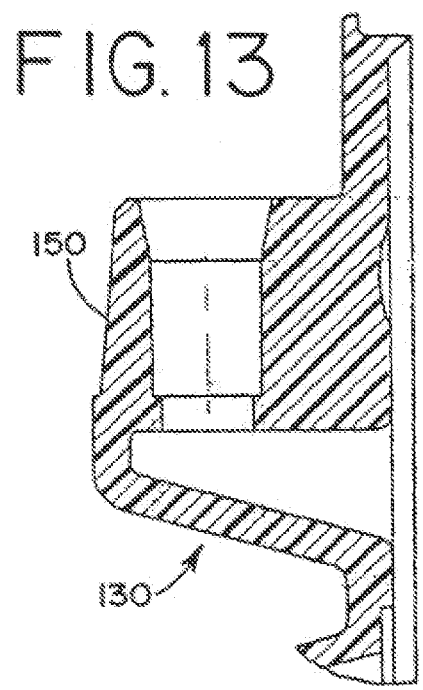
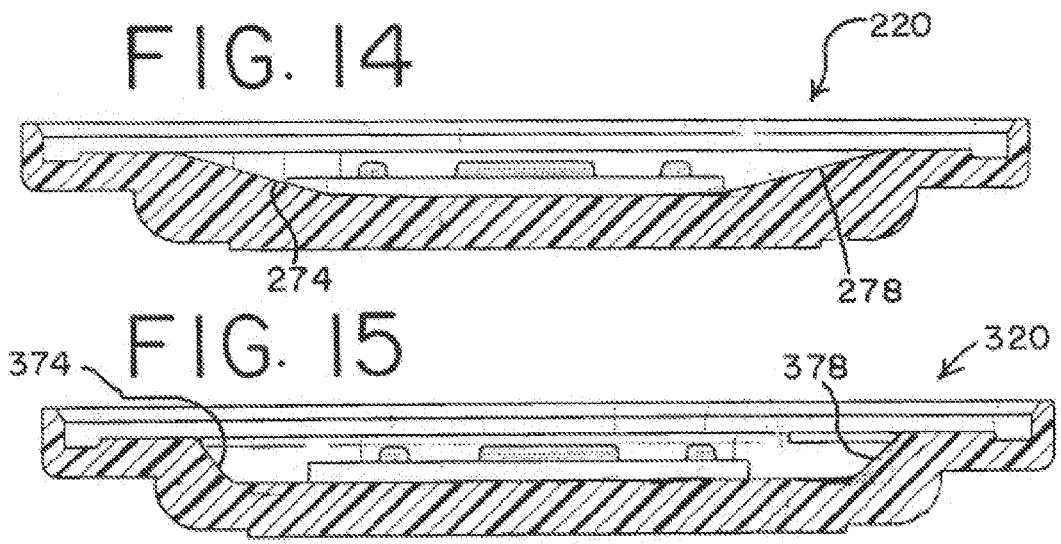

BACTERIAL RETENTIVE, AIR VENTING, INTRAVENOUS FILTER

REFERENCE TO RELATED APPLICATION

The present application claims the benefit of the filing date under 35 U.S.C. § 119(e) of Provisional U.S. patent application Ser. No. 60/440,106, filed Jan. 15, 2003, which is hereby incorporated by reference in its entirety.

BACKGROUND OF THE INVENTION

This invention pertains to the field of membrane-type filter devices, particularly intravenous filter devices which employ both hydrophilic and hydrophobic membranes.

This invention relates broadly to membrane-type filter devices, and especially to filter devices used to remove impurities from liquids or fluids that are to be introduced intravenously to the human body. Some fluids useful with this invention include saline solutions and nutrient solutions, or other solutions that act as carriers for drugs. Other fluids useful with this invention are not listed but are well known to those having ordinary skill in the art.

One of the problems encountered with conventional membrane-type intravenous filter devices is the presence of gas. The fluid must be filtered before entering the patient in order to remove gas bubbles and contaminants. Gas in the housing or mixed with the liquid tends to prevent effective filtration of the liquid. When the filter is first attached to the patient and fluid flow is initiated, air frequently enters the lines or is already present in the filter device. A wetted hydrophilic membrane filter will generally not allow the air to pass. Thus, entrapped air tends to prevent fluid from entering the patient. It is therefore desirable to remove this entrapped air as quickly and continuously as possible. This is often referred to as priming the filter.

Several options are available to remove air from membrane-type filter devices. Many of these options make use of hydrophobic membranes which are capable of passing air out of the filter housing through vents, but liquids will not pass through the membranes. Conventional intravenous filters employ this principle but have some shortcomings. For example, several commercial devices are not altogether satisfactory because they do not remove air through the outlet port in the short time that is necessary, or they require the filter to be turned upside down, or in an orientation different than how the filter will be used, during priming. This can lead to confusion and a lack of proper priming, leaving gas entrapped in areas of the housing that are not contiguous to the hydrophobic membrane.

Various ideas have been used in an attempt to correct these shortcomings. Some manufactures utilize rectangular filters to assist self-priming, with an inlet at the bottom and an outlet at the top of the filter. Such devices must be tilted from a horizontal plane in order to be self-priming. Some do not utilize a hydrophobic-type filter medium. Still other filter units employ a combination of hydrophilic and hydrophobic filters arranged side-by-side in alternate sequence. A disadvantage, however, is that this configuration provides a hydrophobic zone on each end of the housing. Although these chambers appear to provide for the escape of entrapped air, they also create a zone where liquids can gather and be incapable of passing through either the hydrophilic membrane or the hydrophobic membrane. Further, drugs in intravenous fluids often have different densities than other fluids administered to the patient. This may mean that the drugs will be in a portion of the filter adjacent a hydrophobic membrane if the filter unit is in a vertical position. When this is the case, the drugs may not immediately be administered to the patient. This could conceivably cause problems, especially if drugs must be administered quickly to the patient.

One product, known as the Gelman IV-4 filter, has two vent holes on the back side so as to allow venting from two places in the inlet chamber. However, there are increased manufacturing costs from having to seal two hydrophobic membranes while constructing the filter, plus this design doubles the possibility of a defective filter due to a leak if the hydrophobic material is not correctly sealed.

Another problem is that support ribs, used to hold the filtration media away from the wall of the filter housing, create many small flow channels. Small bubbles can form in these channels during priming and, even though the filter is properly oriented, the bubbles may stay trapped in the narrow ends of the channels and not be flushed out the outlet port.

An additional problem is that many filters have tubing connections that orient the filter in such a manner that if the filter is suspended from an intravenous fluid source, with additional tubing suspended therefrom, the filter either does not hang so that the vent is properly positioned, or the weight of the filter, or tension on the tubing if the patient pulls on the tubing, causes the filter to tip to one side and kink the tubing.

The problems enumerated in the foregoing are not intended to be exhaustive but rather are among many which tend to impair the effectiveness of previously known filter devices. Other noteworthy problems may also exist; however, those presented above should be sufficient to demonstrate that filter devices appearing in the art are not altogether satisfactory.

U.S. Pat. No. 5,827,429 discloses an IV filter that overcomes many of the foregoing disadvantages. The commercial embodiment of the inventive filter of the '429 patent has one hydrophobic media with two air vent holes. Both of these holes exit on the front side of the filter under the inlet to the filter where hopefully they would not be blocked if someone taped the filter onto a surface. However, even this design has some room for improvement.

BRIEF SUMMARY OF THE INVENTION

This invention is based on the discovery of a continuously venting, self-priming filter device. Although the filter device of the present invention may be used for filtering a wide variety of fluids, its main usefulness is for medical and diagnostic purposes, i.e., intravenous filter devices. This is because quick self-priming and continuous venting is particularly important for intravenous applications. A surprising advantage of this invention is that the shape of the inlet chamber, particularly in conjunction with the location of the tubing connectors and the vent, assists the filter device in quickly purging air during priming while the filter is in the position of its intended use, and continuously venting gases entrapped in the chamber during use.

In one aspect, the invention is a filter for filtering intravenous fluid comprising a base member having an outer perimeter, one or more vent holes and a fluid inlet chamber; a cap member having an outer perimeter, an inlet, an outlet and a fluid outlet chamber; generally planar hydrophilic filtration media mounted between the base member and the cap member, separating the inlet chamber and the outlet chamber; the perimeters of the base and cap members being sealed together to form a filter housing, and the filter having a flow path such that fluid passing into the filter housing through the inlet passes through the hydrophilic filtration media before passing out of the outlet; one piece of hydrophobic vent media positioned over the one or more vent holes and secured to the base member; and the base member having a center section and side sections forming the inlet chamber, the side sections extending from the center section towards the perimeter of the base member and being formed at an angle of between 2° and about 45° compared to the plane of the hydrophilic filtration media so as to encourage any air in the inlet chamber to flow towards the vent.

In another aspect, the invention is in a filter for filtering intravenous fluid having a base member and a cap member sealed together to form a filter housing, hydrophilic filtration media secured within the housing, the hydrophilic filtration media separating the filter housing into a fluid inlet chamber and a fluid outlet chamber, the filter housing having an inlet and an outlet in fluid communication with the inlet chamber and outlet chamber respectively, the housing being generally flat and rectangular, and the housing being vented through hydrophobic vent media, the improvement comprising: the inlet chamber having only one vent, and the base member having sloped walls on interior surfaces providing the inlet chamber with a contoured shape to encourage any air within the inlet chamber to flow toward the vent.

The filter of the present invention is vented and self priming. In the preferred embodiment the single vent is located opposite the inlet. In the preferred embodiment, the filter is light weight and the tubing connectors are positioned and aligned so that, when suspended in an I.V. set, the filter and tubing hang straight without any tendency to kink, and the vent is located near the top of the filter. Also, the preferred embodiment vent, inlet and outlet locations allow the filter to be primed with the filter in the same orientation in which it is intended to be used.

These and other advantages of the invention, as well as the invention itself, will be better understood in view of the accompanying drawings.

BRIEF DESCRIPTION OF SEVERAL VIEWS OF THE DRAWINGS

FIG. 1 is a perspective view of a preferred filter in accordance with the present invention.

FIG. 2 is an exploded view of the components making up the filter of FIG. 1.

FIG. 3 is a plan view of the inside surface of the base member of the filter of FIG. 1.

FIG. 4 is a plan view of the inside surface of the cap member of the filter of FIG. 1.

FIG. 5 is an enlarged cross-sectional view taken along line 5—5 of FIG. 3.

FIG. 6 is a cross-sectional view taken along line 6—6 of FIG. 4.

FIG. 7 is a cross-sectional view taken along line 7—7 of FIG. 4.

FIG. 8 is a cross-sectional view taken along line 8—8 of FIG. 1.

FIG. 9 is an enlarged cross-sectional view taken along line 9—9 of FIG. 3.

FIG. 10 is a cross-sectional view of a base of a prior art filter, similar to the view of FIG. 8.

FIG. 11 is another cross-sectional view of the base of the prior art filter of FIG. 10, similar to the view of FIG. 5.

FIG. 12 is a plan view of a second embodiment filter of the present invention.

FIG. 13 is an enlarged cross-sectional view taken along line 13—13 of FIG. 12.

FIG. 14 is a cross-sectional view like FIG. 5 of a third embodiment filter of the present invention.

FIG. 15 is a cross-sectional view like FIG. 5 of a fourth embodiment filter of the present invention.

DETAILED DESCRIPTION OF THE INVENTION

FIGS. 1–9 show a new filter for filtering intravenous fluid in accordance with the present invention. This particular filter, which is the preferred embodiment, comprises a generally flat, vented housing 10 which comprises a fluid inlet chamber 12 and a fluid outlet chamber 14 separated by a hydrophilic filtration media 40 (FIG. 8). This filter comprises a back housing part, referred to as base member 20; a front housing part, referred to as cap member 30; the hydrophilic filtration media 40 and a hydrophobic vent membrane 45 (FIG. 2). Each of the base and cap members 20, 30 include an outer perimeter. These outer perimeters are sealed together to form the housing 10.

As can be seen in FIG. 8, and the hydrophilic filtration media 40 is generally planar, and secured within the housing, separating the housing into the fluid inlet chamber 12 and the fluid outlet chamber 14. Preferably, the housing 10 is transparent and the base and cap members are generally rectangular. An inlet to the housing delivers fluid to the inlet chamber 12. An outlet delivers fluid from the outlet chamber. 14 after the fluid has passed through the media 40. The device also comprises a single vent hole 52 for releasing entrapped gas from the inlet chamber.

The inlet to the housing 10 comprises an inlet tubing connector 50. The outlet of the housing 10 comprises an outlet tubing connector 60. As shown in FIGS. 1, 2 and 8, preferably the inlet and outlet tubing connectors 50, 60 are placed near to each other but facing in opposite directions with respect to each other, with the inlet tubing connector facing the first or top end 16 of the housing and the outlet tubing connector 60 facing the second or bottom end 18 of the housing. The inlet and outlet connectors 50, 60 are preferably located adjacent the first end 16 of the housing 10, and are spaced inwardly of the housing ends. The filter has a flow path such that fluid passing into the filter housing through the inlet passes through the hydrophilic filtration media before passing out of the outlet.

Preferably the connectors 50, 60 are raised above the surface of the front side of the housing 10 such that tubing connected to the connectors does not intersect the front side of the housing 10. For male tubing connectors, as shown, this means that tubing connected to the connectors will fit onto the connectors without any substantial interference with the surface of the front side of the housing. If female connectors were used (see FIGS. 12–13), instead of the male connectors shown, this means that the bottom of the inside connecting surface would be above the plane of the filter housing front side. By having the tubing connectors raised to such a substantial height, the profile of the front side of the filter housing 10 is such that it will not be mistakenly placed against the arm of a patient. Instead, the back side of the filter housing 10, which is generally flat, will be placed against the patient's arm or other support surface. The back surface does, however, include a standoff 92 that extends over most of the back except in the area around the vent hole. The stand-off is semi-circular in the region 94 surrounding the vent hole 52. The standoff 92 thus elevates the filter slightly so that the vent hole 52 is not blocked if the filter is placed on a flat surface or taped to a patient's arm.

The preferred filter housing 10 is symmetrical about a plane that intersects the tubing connectors 50, 60 and is normal to the plane of the hydrophilic filtration media. Also, the tubing connectors are preferably in line with one another. In this regard, the filter is then evenly balanced side to side so that when the filter is suspended from an intravenous fluid source, the filter hangs straight up and down and does not cause kinks in the tubing. The filter is designed to contain less plastic, and thus be lighter in weight, than prior art filters, helping to prevent kinking without the need for tubing clip. For example, the preferred filter only weighs 8.7 grams, but includes about 1.82 in$^2$ (1175 mm$^2$) of effective filtration surface area, which is a ratio of 0.0074 g/mm$^2$. Preferred filters of the present invention will have a ratio of weight of the filter to filtration surface area of less than 6 grams/in$^2$ (0.0093 g/mm$^2$), and more preferably less than about 5 grams/in$^2$ (0.00775 g/mm$^2$). A commercial embodiment of the filter disclosed in U.S. Pat. No. 5,827,429 weighed 13.5 grams and had about 1450 mm$^2$ effective filtration surface area, which is a ratio of 0.0093 g/mm$^2$.

As best seen in FIG. 8, fluid enters the filter housing 10 through inlet tubing connector 50. An inlet channel 54 allows the fluid to pass to the inlet chamber 12, which is located adjacent the back side of the filter housing 10. The inlet channel 54 delivers fluid into the chamber 12 at a point in line with and directly opposite the vent hole 52. In that regard, the fluid flow entering the inlet chamber 12 is directed toward the vent media. Gas bubbles entering the chamber 12 will contact the hydrophobic membrane 45 and exit vent hole 52. Fluid will be able to reach the hydrophilic filtration media 40 and pass there through. Because of the location of the inlet channel 54 and the shape of the inlet chamber, it is believed that only one hydrophobic vent membrane will be necessary for proper operation of the filter, thus simplifying production and reducing the possibility of leaks which can occur when vent materials are not properly sealed.

Preferably there is only one vent hole 52, and it is located at one end of the inlet chamber 12. In the preferred embodiment, the vent hole is open to the back side of the filter housing 10 and positioned generally opposite the inlet 54. Also, in the preferred embodiment, the vent hole 52 is in direct communication with a single hydrophobic membrane member 45, which preferably has a round shape as shown in FIG. 2. The vent hole 52 is located on a center line parallel to the length of the base member 20 and approximately at a point along that center line that is between the beginnings of the bevels on the corners of the housing.

As best seen in FIG. 8, fluid enters the filter housing 10 through inlet tubing connector 50. An inlet channel 54 allows the fluid to pass to the inlet chamber 12, which is located adjacent the back side of the filter housing 10. The inlet channel 54 delivers fluid into the chamber 12 at a point in line with the vent hole 52. Gas bubbles entering the chamber 12 will contact the hydrophobic membrane 45 and exit vent hole 52. Fluid will be able to reach the hydrophilic filtration media 40 and pass there through. Because of the location of the inlet channel 54 and the shape of the inlet chamber, it is believed that only one hydrophobic vent membrane will be necessary for proper operation of the filter, thus simplifying production and reducing the possibility of leaks which can occur when vent materials are not properly sealed.

As best seen in FIGS. 3, 5 and 8, the fluid inlet chamber 12 formed in base member 20 is rectangular in shape, but has sloped walls on its interior surface providing the inlet chamber with a contoured shape to encourage any air within the inlet chamber to flow toward the vent hole 52. The inside surface of the base member 20 has a center section 72 and three side sections that form the inlet chamber. The three side sections extend from the center section 72 towards the perimeter. One of the side sections is formed adjacent each of the two long sides 13 and the first end side 18. The three side sections end at a ledge inside the shoulder 82, just inside the perimeter of the filter. This shoulder 82 is used to clamp the hydrophilic filtration media when the cap and base members are assembled. FIG. 5 shows the preferred contour. In this preferred contour, the sloped walls of the interior surface of the inlet chamber actually have both an angled section 74, 76, 78 and a curved section 84, 86, 88. The angle 79 of the angled sections will be between about 2° and about 45° compared to the plane of the hydrophilic media. The angle 79 is preferably between about 5° and about 30°, more preferably between about 5° and 10°, and most preferably about 7.5° when a curved or steeper angled section is also used. In this preferred embodiment, the curved sections 84, 86 and 88 each have a radius of about 0.3 inches.

The contoured surface of the present invention is contrasted with a prior art filter shown in FIGS. 10 and 11, which are believed to show the inside shape of the Gelman IV-4 filter. The base 200 of that filter included two vent holes 212, each covered with a separate piece of hydrophobic vent media, and did not have any contoured shape. Instead, the base 200 had a shoulder 214 that the filtration media was secured to, and then nearly vertical walls down to the inside surface of the base 200, with a sharp corner at the juncture of the walls and the base.

After passing through inlet chamber and being filtered by the hydrophilic filtration media 40, fluid enters outlet chamber 14 and is directed towards outlet tubing connector 60. The connector 60 is preferably at the top of outlet chamber 14 when the filter is oriented as shown in FIG. 1. In this orientation, the filter is self priming, as any gas in the outlet chamber will rise as fluid enters the outlet chamber through filtration media 40.

The flow path downstream of the filtration media 40 preferably includes flow channels created by a plurality of ridges 25 molded onto the inside of the front housing part 30. (FIGS. 4, 6 and 7.) The ridges 25 support the filtration media 40 against pressure exerted by the fluid trying to pass through the media 40. The ridges 25 run in a direction from the second end 18 of the housing 10 toward the outlet 64, parallel to the long side of the housing, and run up the inside of one wall 31 forming the outlet 64. Another set of ridges 27 (FIGS. 4 and 8) are formed on a second wall 29 forming the outlet 64, and extend toward the bottom 18. The ridges 25, and the ridges 27, are preferably spaced at least 1 mm apart from one another to prevent air bubbles from getting stuck between the ridges. In the preferred embodiment shown in FIG. 7, the spacing between the ridges is 0.05 inches (1.27 mm).

The methods and essential materials for making the housing 10 are well known in the art and generally involve the use of clear synthetic resins. The overall size of the housing 10 is generally well known and is not substantially different from conventional intravenous filter devices. The preferred device, shown in FIGS. 1–9, should have a void volume of less than about 2.7 ml, and preferably has a void volume of about 2.6 ml or less. Generally speaking, for intravenous applications, smaller filters are preferred over larger filters. A smaller filter is lighter and more convenient for the patient. Furthermore, the low void volume of a smaller filter means there is a smaller hold-up volume than with a larger filter; that is, there is less liquid remaining in the filter device at any given time. Low hold-up volume in intravenous filters is especially preferred for low administration rates. Low void volume also helps the filter prime more quickly.

The filter housing 10 could be constructed of flexible material such as polypropylene, polyethylene or polyvinyl chloride. However, because visibility is desirable, the preferred embodiment is made from a substantially transparent material. A transparent filter provides visibility such that the fluid to be filtered can be readily seen by the patient, doctor or medical attendant. Thus, a gas bubble, foreign object or liquid contaminant blocking a portion of the hydrophilic membrane can be readily detected. Accordingly, a preferred material is an impact-modified acrylic such as acrylonitrile butadiene styrene terpolymer or any other plastic material that is durable, transparent and not unduly brittle. Materials such as polypropylene and polyethylene are less transparent and thus normally less preferred. However, a less transparent but more durable material may be preferred if high fluid pressures are to be employed.

During assembly, a circular piece of hydrophobic vent media 45 is first secured to cover vent hole 52 in base member 20. The vent hole 52 is surrounded by a vent media securement shoulder 56 which is circular in shape. As can be seen in FIG. 9, the fluid inlet chamber 12 extends only on a first side of the vent media securement shoulder. The base member 20 has an elevation 59 on the second side such that the elevation 59 fits against the cap member 30 (FIG. 8). A plurality of locating ribs 58 are formed on the vent media securement shoulder. The ribs are configured to help center the hydrophobic vent media over the vent hole 52 during a manual assembly process. The hydrophobic vent media 45 is secured to the base member by a heat sealing process. The hydrophilic filtration media 40 is also heat sealed to the cap member 30. A heated die is used to seal these materials to their respective housing members 20 and 30.

The housing 10 of the present invention can be made by sealing the base and cap members 20 and 30 together to form a cavity. The members 20, 30 are sealed by conventional techniques. Any workable method of sealing the device against leakage is contemplated, including radio frequency weld sealing, hot melt sealing, ultrasonic sealing or solvent sealing. Although several methods of sealing are within the scope of the invention, it has been found that ultrasonic weld sealing is preferred for acrylic materials. In this embodiment, each housing member 20, 30 has a flange about its rim that fits to the flange of the other housing member.

The hydrophilic filtration media 40 and hydrophobic membrane 45 of the present invention are well known in the art. The preferred material for the hydrophobic membrane 45 is a polyester-supported PTFE having PTFE membrane attached to a polyester fibrous pad by a polyester adhesive. The preferred membrane 45 is manufactured by W. L. Gore & Associates, Elkton, Md., having a 0.02 micron pore size.

The media 40 can be made of polyethersulfone, a PVC, acrylic copolymer, polysulfone, polyvinylidene fluoride, cellulose acetate, cellulose nitrate, mixed esters of cellulose, nylon or polyamide. The hydrophilic media 40 is microporous, and the mean pore size of the media is from about 0.2 micron to about 150 microns. The most preferred mean pore size is about 0.22 micron. A preferred material for the media 40 is Magna PES membrane, made from polyethersulfone, by Osmonics, Minnetonka, Minn. Another membrane that may be used is MicroPES from Membrana GmbH of Wuppertal, Germany. It is available in both a 0.2 micron (MicroPES 2F iv) and a 1.2 micron rating (MicroPES 12F iv). The micron rating selected depends on the application.

The media 40 is shaped to fit the housing 10, being large enough for its edges to be sealed to be substantially leak proof. The media 40 surface area of the presently preferred embodiment is about 1.82 in$^2$ (1175 mm$^2$). The preferred embodiment utilizes the smallest surface area possible so that a more economical unit can be produced at a reduced cost. For a unit having a hydrophilic media 40 surface area of about 1.82 square inches, the unit has a preferred flow rate range of from about 25 ml to about 50 ml, more preferably about 30 ml, per minute at 1 psig. The operating fluid pressure range is from about 1 psig to about 5 psig.

Although the preferred housing 10 is flat, the shape is not critical. Although in this embodiment, the top corners are beveled, they may also be rounded like the bottom corners, depending on aesthetic preference, desired shape and economics in molding. Such non-rectangular corners reduce the tendency of gas bubbles to occupy the corners of the chamber and thus avoid contacting the hydrophobic membrane 45 covering vent hole 52.

By having the inlet connector 50 and outlet connector 60 close to one another, the inlet and outlet channels 54 and 64 can also be close together. Preferably the connectors 50 and 60 are only a few millimeters apart.

By having the inlet connector 50 and outlet connector 60 both attached to the cap member 30, the base member 20 has a fairly simple design and can be easily molded. The cap member 30 is preferably molded with the connectors 50, 60 as one monolithic part with the rest of the cap, though other methods of attaching these items could be used.

A second embodiment, shown in FIGS. 12 and 13, uses female tubing connectors, but is otherwise the same as filter 10. The cap member 130 of filter 110 has the same shape as cap member 30, except that the inlet and outlet tubing connectors 150 and 160 are designed to fit the outside diameter of IV set tubing rather than the inside diameter. FIG. 13 shows an enlarged cross-sectional view of the female inlet tubing connector 150.

The slope on the inside sections of the inlet chamber encourages any air in the inlet chamber to flow towards the vent. The elevation 59 on the opposite side of the vent media securement shoulder prevents fluid from flowing into the filter housing on that end of filter housing.

FIGS. 14 and 15 show two additional embodiments of base members 220 and 320 that could be used in making the invention, in which the contoured shape of the inlet chamber is made by different angled surfaces. In the base member 220 shown in FIG. 14, the sloped walls are made of fairly long angled sections 274 and 278. In base member 320 shown in FIG. 15, the angled sections 374 and 378 are shorter and their angle is steeper. Of course the sloped wall could be formed entirely of a curved surface, as wall as different combinations of curved and angled surfaces. The important feature in all of these embodiments is that the inlet chamber is contoured so that any air bubbles will tend to be pushed along towards the vent hole 52 and does not have corners where air bubbles can be trapped. In the prior art Gelman IV-4, air bubbles could just stay in the corners formed at the base and side walls of the inlet housing member. With the present design, the fluid dynamics helps push the air towards the center and hence to the vent, rather than collecting at the periphery. On other hand, the sloped surface should not be so shallow that fluid cannot easily contact the entire surface of the filter media. In addition, a flat slope increases the amount of plastic in the filter, and hence its weight and cost. Thus, if a shallow angle less than 10° is used, preferably there is also another steeper or curved section, as in the embodiment of FIG. 5, so that the fluid can easily contact the entire media.

The preferred embodiment incorporates many features, not all of which are necessary for achieving some of the benefits of the present invention. For example, multiple vent holes 52 in close proximity to one another could all be used to remove air passing through a single piece of vent media. The avoidance of having to seal multiple pieces of vent media would still be met with a single vent having multiple outlet holes. Also, while a preferred embodiment of the filter has been shown, many variations are possible. For example, support ribs could be provided on the base member 20 to support the filtration media 40 against back pressure when the filter is to be used on devices that produce a back pressure. The locating ribs 58 may be done away with in methods of assembly in which the hydrophobic membrane is located on the vent media securement shoulder by automated equipment.

It should be appreciated that the products of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

The invention claimed is:

1. A filter for filtering intravenous fluid comprising:
a) a base member having an outer perimeter, one or more vent holes and a fluid inlet chamber;
b) a cap member having an outer perimeter, an inlet, an outlet and a fluid outlet chamber, wherein the one or more vent holes are positioned generally opposite the inlet;
c) generally planar hydrophilic filtration media mounted between the base member and the cap member, separating the inlet chamber and the outlet chamber;
d) the perimeters of the base and cap members being sealed together to form a filter housing, and the filter having a flow path such that fluid passing into the filter housing through the inlet passes through the hydrophilic filtration media before passing out the outlet;
e) one piece of hydrophobic vent media positioned over the one or more vent holes and secured to the base member; and
f) the base member having a center section and side sections forming the inlet chamber, the side sections extending from the center section towards the perimeter of the base member and being formed at an angle of between about 2° and about 45° compared to the plane of the hydrophilic filtration media so as to encourage any air in the inlet chamber to flow towards the vent.

2. The filter of claim 1 wherein the base member has a shoulder inside of the perimeter which clamps against the hydrophilic filtration media when the base and cap members are assembled, and a ledge inside of the shoulder, and wherein the side sections of the base member extend between the center section and the ledge.

3. A filter for filtering intravenous fluid comprising:
a) a base member having an outer perimeter, one or more vent holes and a fluid inlet chamber;
b) a cap member having an outer perimeter, an inlet, an outlet and a fluid outlet chamber, wherein the filter cap and base members each have a generally rectangular shape with two beveled corners, the beveled corners forming a generally triangular region;
c) generally planar hydrophilic filtration media mounted between the base member and the cap member, separating the inlet chamber and the outlet chamber;
d) the perimeters of the base and cap members being sealed together to form a filter housing, and the filter having a flow path such that fluid passing into the filter housing through the inlet passes through the hydrophilic filtration media before passing out the outlet;
e) one piece of hydrophobic vent media positioned over the one or more vent holes and secured to the base member; and
f) the base member having a center section and side sections forming the inlet chamber, the side sections extending from the center section towards the perimeter of the base member and being formed at an angle of between about 2° and about 45° compared to the plane of the hydrophilic filtration media so as to encourage any air in the inlet chamber to flow towards the vent.

4. The filter of claim 3 wherein the generally rectangular shape is formed of six sides, with two long sides each parallel to one another, and each having first and second ends, a first end side perpendicular to the two long sides and spanning between the first ends of the two long sides, and the generally triangular region being opposite to the first end side and made up of a short second end side and two angled sides each extending between the second end of one of the long sides and the second end side.

5. The filter of claim 3 wherein the vent hole is located on a center line parallel to the length of the base member and at approximately a point along the center line that is between the beginnings of the bevels on the corners.

6. The filter of claim 4 wherein there are three base member side sections, one formed adjacent the first end side and the other two each formed adjacent one of the long sides.

7. The filter of claim 1 wherein the vent hole is surrounded by a vent media securement shoulder against which the hydrophobic vent media is secured.

8. A filter for filtering intravenous fluid comprising:
a) a base member having an outer perimeter, one or more vent holes and a fluid inlet chamber;
b) a cap member having an outer perimeter, an inlet, an outlet and a fluid outlet chamber;
c) generally planar hydrophilic filtration media mounted between the base member and the cap member, separating the inlet chamber and the outlet chamber;
d) the perimeters of the base and cap members being sealed together to form a filter housing, and the filter having a flow oath such that fluid passing into the filter housing through the inlet passes through the hydrophilic filtration media before passing out the outlet;
e) one piece of hydrophobic vent media positioned over the one or more vent holes and secured to the base member, wherein the vent hole is surrounded by a vent media securement shoulder against which the hydrophobic vent media is secured; and
f) the base member having a center section and side sections forming the inlet chamber, the side sections extending from the center section towards the perimeter of the base member and being formed at an angle of between about 2° and about 45° compared to the plane of the hydrophilic filtration media so as to encourage any air in the inlet chamber to flow towards the vent;

g) wherein the fluid inlet chamber extends only on a first side of the vent media securement shoulder, the base member having an elevation of a second side of the vent media securement shoulder such that the base member elevation fits against the cap member, thereby preventing fluid from flowing into the filter housing on the second side of the vent media securement shoulder.

9. The filter of claim 8 wherein the vent media securement shoulder is circular in shape.

10. A filter for filtering intravenous fluid comprising:
a) a base member having an outer perimeter, one or more vent holes and a fluid inlet chamber;
b) a cap member having an outer perimeter, an inlet, an outlet and a fluid outlet chamber;
c) generally planar hydrophilic filtration media mounted between the base member and the cap member, separating the inlet chamber and the outlet chamber;
d) the perimeters of the base and cap members being sealed together to form a filter housing, and the filter having a flow path such that fluid passing into the filter housing through the inlet passes through the hydrophilic filtration media before passing out the outlet;
e) one piece of hydrophobic vent media positioned over the one or more vent holes and secured to the base member, wherein the vent hole is surrounded by a vent media securement shoulder against which the hydrophobic vent media is secured; and
f) the base member having a center section and side sections forming the inlet chamber, the side sections extending from the center section towards the perimeter of the base member and being formed at an angle of between about 2° and about 45° compared to the plane of the hydrophilic filtration media so as to encourage any air in the inlet chamber to flow towards the vent;
g) wherein the vent media securement shoulder further comprises a plurality of locating ribs configured to help center the hydrophobic vent media over the vent hole during assembly of the filter.

11. In a filter for filtering intravenous fluid having a base member and a cap member sealed together to form a filter housing, hydrophilic filtration media secured within the housing, the hydrophilic filtration media separating the filter housing into a fluid inlet chamber and a fluid outlet chamber, the filter housing having an inlet and an outlet in fluid communication with the inlet chamber and outlet chamber respectively, the housing being generally flat and rectangular, and the housing being vented through hydrophobic vent media, the improvement comprising:
a) an inlet chamber having only one vent, and
b) the base member having sloped walls on interior surfaces providing the inlet chamber with a contoured shape to encourage any air within the inlet chamber to flow toward the vent.

12. The improved filter of claim 11 wherein the inlet chamber is generally rectangular in shape and the one vent is located at one end of the inlet chamber.

13. The improved filter of claim 11 wherein the one vent is located in the base member opposite to the inlet into the filter housing.

14. The improved filter of claim 11 wherein the housing forming the fluid outlet chamber includes a plurality of ridges extending generally parallel with the long side of the rectangular housing.

15. The improved filter of claim 14 wherein the ridges have an average spacing of at least 1 mm between them.

16. The improved filter of claim 11 wherein the ratio of the weight of the filter to the surface area of the hydrophobic filtration media is less than about 6 grams/in$^2$.

17. A filter for filtering intravenous fluid comprising:
a) a base member having an outer perimeter, one or more vent holes and a fluid inlet chamber;
b) a cap member having an outer perimeter, an inlet with an inlet tubing connector, an outlet with an outlet tubing connector, and a fluid outlet chamber;
c) generally planar hydrophilic filtration media mounted between the base member and the cap member, separating the inlet chamber and the outlet chamber;
d) the perimeters of the base and cap members being sealed together to form a filter housing, the filter housing having first and second ends, and the filter having a flow path such that fluid passing into the filter housing through the inlet passes through the hydrophilic filtration media before passing out the outlet, wherein the inlet tubing connector faces the first end of the filter housing and the outlet tubing connector faces the second end of the filter housing;
e) one piece of hydrophobic vent media positioned over the one or more vent holes and secured to the base member; and
f) the base member having a center section and side sections forming the inlet chamber, the side sections extending from the center section towards the perimeter of the base member and being formed at an angle of between about 2° and about 45° compared to the plane of the hydrophilic filtration media so as to encourage any air in the inlet chamber to flow towards the vent.

18. The filter of claim 1 wherein the inlet and outlet both comprises tubing connectors, and wherein the tubing connectors are in line with one another.

19. A filter for filtering intravenous fluid comprising:
a) a base member having an outer perimeter, one or more vent holes and a fluid inlet chamber;
b) a cap member having an outer perimeter, an inlet with an inlet tubing connector, an outlet with an outlet tubing connector, and a fluid outlet chamber;
c) generally planar hydrophilic filtration media mounted between the base member and the cap member, separating the inlet chamber and the outlet chamber;
d) the perimeters of the base and cap members being sealed together to form a filter housing, the filter housing having first and second ends, and the filter having a flow path such that fluid passing into the filter housing through the inlet passes through the hydrophilic filtration media before passing out the outlet, wherein the tubing connectors are spaced inwardly of the first and second ends of the housing;
e) one piece of hydrophobic vent media positioned over the one or more vent holes and secured to the base member; and
f) the base member having a center section and side sections forming the inlet chamber, the side sections extending from the center section towards the perimeter of the base member and being formed at an angle of between about 2° and about 45° compared to the plane of the hydrophilic filtration media so as to encourage any air in the inlet chamber to flow towards the vent.

20. The filter of claim 1 wherein the vent media is directly opposite the inlet.

21. The filter of claim 1 wherein the fluid flow entering the inlet chamber is directed toward the vent media.

* * * * *

UNITED STATES PATENT AND TRADEMARK OFFICE
CERTIFICATE OF CORRECTION

PATENT NO.       : 7,141,097 B2
APPLICATION NO.  : 10/755980
DATED            : November 28, 2006
INVENTOR(S)      : John A. Leahey It is certified that error appears in the above-identified patent and that said Letters Patent is hereby corrected as shown below:

<u>On the Title Page</u>

In column 1, under "Notice", after "U.S.C. 154(b) by" delete "123" and substitute --177-- in its place.

In column 1, line 1, under "U.S. PATENT DOCUMENTS", delete "Sloane et al." and substitute --Sloane, Jr. et al.-- in its place.

<u>In the Claims</u>

Column 10, in claim 8, line 11, after "having a flow" delete "oath" and substitute --path-- in its place.

Signed and Sealed this

Twenty-ninth Day of January, 2008

JON W. DUDAS
*Director of the United States Patent and Trademark Office*